(12) United States Patent
Andreacchi et al.

(10) Patent No.: US 8,815,061 B2
(45) Date of Patent: Aug. 26, 2014

(54) ELECTROPOLISHING FIXTURE WITH PLUNGER MECHANISM

(75) Inventors: Anthony S. Andreacchi, San Jose, CA (US); Sophia L. Wong, Milipitas, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 35 days.

(21) Appl. No.: 13/618,348

(22) Filed: Sep. 14, 2012

(65) Prior Publication Data

US 2014/0076737 A1    Mar. 20, 2014

(51) Int. Cl.
*C25F 3/16* (2006.01)
*C25F 7/00* (2006.01)
*A61F 2/82* (2013.01)

(52) U.S. Cl.
CPC ... *C25F 3/16* (2013.01); *C25F 7/00* (2013.01); *A61F 2/82* (2013.01)
USPC .................................. 204/224 M; 205/640

(58) Field of Classification Search
USPC .................................................... 204/224 M
See application file for complete search history.

(56) References Cited

U.S. PATENT DOCUMENTS

| 7,252,746 | B2 * | 8/2007 | Schaeffer .................. 204/224 M |
| 2004/0267351 | A1 * | 12/2004 | Swain .......................... 623/1.15 |
| 2005/0098444 | A1 | 5/2005 | Schaeffer |
| 2007/0034527 | A1 * | 2/2007 | Diaz et al. ..................... 205/686 |
| 2007/0034528 | A1 | 2/2007 | Diaz et al. |
| 2007/0209947 | A1 | 9/2007 | Shrivastava et al. |
| 2008/0312747 | A1 | 12/2008 | Cameron et al. |
| 2009/0255827 | A1 * | 10/2009 | Andreacchi et al. .......... 205/640 |
| 2012/0199489 | A1 | 8/2012 | Vacheron |

FOREIGN PATENT DOCUMENTS

JP    H0790694    4/1995

OTHER PUBLICATIONS

U.S. Appl. No. 13/618,407, filed Sep. 14, 2012, Andreacchi.
U.S. Appl. No. 13/617,877, filed Sep. 14, 2012, Andreacchi et al.
U.S. Appl. No. 13/618,455, filed Sep. 14, 2012, Andreacchi et al.
U.S. Appl. No. 13/617,877, Dec. 20, 2013, Office Action.

* cited by examiner

*Primary Examiner* — James Lin
*Assistant Examiner* — Ho-Sung Chung
(74) *Attorney, Agent, or Firm* — Workman Nydegger; Jonathan Feuchtwang

(57) ABSTRACT

An electropolishing fixture with a plunger mechanism. The plunger mechanism can establish contact between a device and an anode mandrel during an electropolishing process while the device is immersed in an electrolytic bath.

24 Claims, 8 Drawing Sheets

ELECTROPOLISHING FIXTURE WITH PLUNGER MECHANISM

BACKGROUND OF THE INVENTION

Medical devices are an important part of the health industry and are responsible for the health of many people. Many life-saving procedures can be performed today because of advances in medical device technology. Stents, for instance, are examples of medical devices that are used in a variety of medical procedures. When stents are used in the context of the vascular system, they can open blocked vessels, increase the flow of blood and prevent reoccurrence of the blockage. Stents are not limited, however, to the vasculature system and can be employed in many systems and circumstances.

The production of medical devices such as stents can be a complicated process. Producing the stent includes forming struts that are arranged to provide strength and flexibility to the stent. The struts can be formed, for example, by laser cutting.

Once the stent is formed, the stent needs to be polished. The stent is polished in order to remove the rough edges that may remain on the stent and to smooth the surface of the stent. As one can image, a stent with rough edges may have adverse effects if introduced into a patient's vasculature. The stent could cut a vessel's wall, for instance, or become inadvertently displaced.

Electropolishing is an example of a method used to polish stents. Electropolishing is a common process that is usually performed by immersing the stents in an electrolytic bath. In conventional systems, however, maintaining a consistent surface finish, particularly along the inner surface of the stent, can be difficult.

More specifically, electropolishing stents requires contact between the stent and an electrode. The contact between the electrode and the stent surface, however, impedes electropolishing at the contact points. As a result, the stent is polished at a different rate at or near the contact points compared to other areas of the stent. There is therefore a need to minimize this effect in order to ensure that surface finish of a stent remains as consistent as possible throughout the electropolishing process.

This process of manufacturing stents is further complicated as the struts become thinner. Thinner struts can make the stent more susceptible to damage. Handling the stent during the electropolishing process becomes more difficult. Because the struts are thinner, it is more challenging to insert, rotate, and remove stents from the anode or mandrel without inadvertently damaging the stent. These problems become more severe as the length of the stents increase. Thus, there is a need for an electropolishing fixture that is easier to load and unload stents or devices and that reduces the risk of damaging the stents or other devices while the stent or device is produced.

BRIEF SUMMARY OF THE INVENTION

Embodiments relate to systems and methods for electropolishing devices including medical devices. More specifically, embodiments relate to an electropolishing fixture configured for electropolishing devices including stents.

In one example, the electropolishing fixture for electropolishing a device includes an actuator and a plunger mechanism. The actuator and the plunger mechanism cooperate to move the plunger mechanism from a retracted position to an extended position. In the extended position, a distal end of the plunger mechanism presses the device against an electrode (e.g., an anode) such that the device can be electropolished.

In another embodiment, the electropolishing fixture includes an actuator and a pair of posts (first post and second post). An electrode (e.g., an anode) is removably connected to contacts extending from each of the posts. A device to be electropolished is loaded on the electrode. The electropolishing fixture includes a plunger mechanism that cooperates with the actuator to move between a retracted position and an extended position relative to the device. In the extended position, the plunger mechanism presses the device against the electrode in the extended position and the device is electropolished in an electrolytic bath.

A method for electropolishing a device such as a stent includes loading the stent on an anode in an electropolishing fixture, immersing the stent in an electrolytic bath, moving a plunger mechanism of the electropolishing fixture to an extended position to establish electrical contact between the stent and the anode, electropolishing the stent, and removing the stent from the electrolytic bath and unloading the stent from the anode.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

The invention will be described and explained with additional specificity and detail through the use of the accompanying drawings in which.

DETAILED DESCRIPTION OF THE PREFERRED EMBODIMENTS

Figure 1:
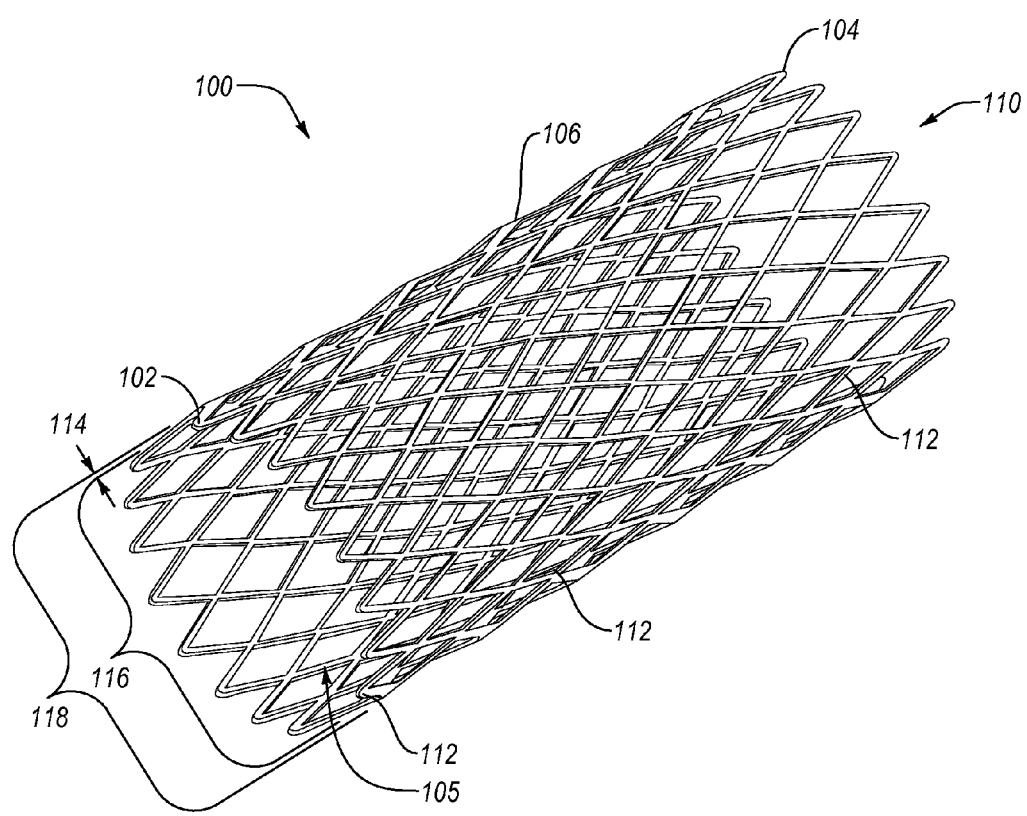
FIG. 1 illustrates a perspective view of a stent, which is an example of a medical device.

Embodiments of the invention relate to systems and methods for electropolishing devices and more particularly to systems and methods for electropolishing medical devices such as stents or the like. Embodiments further relate to systems and methods for establishing or ensuring contact (e.g., electrical contact) between the device and an electrode while the device undergoes an electropolishing process. Ensuring or maintaining electrical contact can prevent arcing and other adverse effects that may damage the device. In addition, the position of the device may be adjusted during the electropolishing process while the device remains immersed. Adjusting the position in this manner can improve the finish and lessen the exposure of the device to an oxidizing environment.

Embodiments establish contact between the electrode and the device in a manner that allows for a wide variety of mandrel (or electrode) designs and configurations and that can minimize damage to the device that may occur during the electropolishing process.

Although embodiments are discussed with reference to a medical device and more particularly in the context of a stent, embodiments are applicable generally to electropolishing systems and methods and to the electropolishing of other devices including other medical devices. During the electropolishing process, the stent is loaded on a mandrel, which may be referred to herein as an electrode (e.g., an anode) since current may be delivered to the stent or other device via the mandrel. As described in more detail herein, the mandrel on which the device is loaded is not required to establish contact (e.g., electrical and/or mechanical contact) with the device even though the effect of gravity may establish such contact.

In accordance with some embodiments, a plunger mechanism is disclosed that operates to establish electrical and/or mechanical contact between the mandrel and the device being electropolished. The plunger mechanism can press the device against the mandrel to form an electrical contact during the electropolishing process. The use of a plunger mechanism can advantageously allow for a wide variety of mandrel (or electrode) designs. Embodiments also improve efficiency by improving device load/unload times while minimizing stent or, more generally, device damage.

Embodiments include an electropolishing system or fixture with a plunger mechanism that cooperates with a mandrel to establish electrical contact during the electropolishing process between the device being electropolished and the mandrel. The electropolishing fixture can be raised and/or lowered into an electrolytic bath. Once the electropolishing fixture is immersed in the electrolytic bath, or once at least the device being electropolished is immersed in the electropolishing bath, the plunger mechanism can be actuated to establish contact between the electrode and the device. The electropolishing fixture may not be completely immersed in the electrolytic bath. Rather, the electropolishing fixture is configured to immerse the device loaded on the electropolishing fixture in the electrolytic bath.

More specifically, a device such as a stent can be placed or loaded onto a mandrel, which operates as an anode. The anode is then removably secured to a pair of posts included in the electropolishing fixture. In one example, the anode is configured to pass through a center of the device. For example, a stent may be placed onto the mandrel by sliding the mandrel through an inner diameter of the stent. The mandrel may be sized and configured to have an effective outer diameter or shape that is smaller than the inner stent diameter. The mandrel can thus fit inside of the stent. The mandrel may loosely fit within the stent. In one embodiment, if the mandrel were held concentrically within the stent, the mandrel would not contact the stent surface. This does not preclude, however, mandrel configurations that contact the stent or that have shapes that are similar to or slightly larger than the inner diameter of the stent.

In an embodiment, an external load or force on the stent brings the stent into contact with the mandrel. For example, gravity may cause the stent or other device to rest on the mandrel. Alternatively, the plunger mechanism may press against the outer stent surface to sandwich the stent between the plunger mechanism (or other object) and the mandrel. The force applied by the plunger mechanism establishes electrical contact between the mandrel and the stent.

Embodiments of the invention contemplate mandrels that may be configured as a substantially straight wire whose diameter is smaller than an inner diameter of the stent. This configuration of the mandrel ensures that a device such as a stent has a loose fit on the mandrel and that the device can be quickly loaded on the mandrel and quickly unloaded from the mandrel. In addition, a loose fit ensures that the struts of the stent are less likely to be damaged during the loading/unloading process.

The mandrel, however, may have a more complex geometry. For example, the mandrel or anode may be shaped to include bends. The mandrel (e.g., a wire) may have a squiggly, coiled, four-point, or other similar geometries that ensure the stent will only contact the mandrel in localized areas when the stent is pressed against the mandrel. In some configurations of the mandrel, an external force may not be required to maintain electrical contact between the stent and the mandrel.

A plunger mechanism is an example of an object that can be advanced and retracted with respect to the mandrel or the stent loaded on the mandrel while the mandrel is secured by lateral posts. When the plunger mechanism is advanced, the plunger mechanism may be brought into contact with the stent to press the stent against the mandrel. In this case, the mandrel may be slightly bowed after the plunger is brought into contact with the stent.

When the mandrel, which holds the stent, is secured by the lateral posts and an electrical contact is formed between the mandrel and the stent, electrical current may be delivered via the lateral posts into the mandrel and the stent. This electrical current drives an electropolishing process when performed within an electrolytic bath.

The posts include contacts that are configured to receive cooperatively configured ends of the mandrel. The plunger mechanism, as well as the contacts of the posts, may be manually moved. Each of the contacts, as well as the plunger mechanism, may be spring loaded such that a spring naturally biases them in one direction. The spring can be manually compressed in order to drive the spring in another direction. Therefore, during the loading and unloading stages of the electropolishing process, the lateral post contacts can be manually biased to enable the mandrel to the connected/disconnected with the contacts. After loading or unloading the stent, the contacts may then be released and allowed to return to their natural position. The mandrel can be tensioned appropriately based on the biasing force of the contacts. In addition, the posts may be received into guides configured to hold the posts in position during the electropolishing process. In one example, the container of the electrolytic bath may include guides to hold the posts of the electropolishing fixture.

In one embodiment, an end of the plunger mechanism may be configured to conform to the stent's contour. For example, because a stent is usually formed as circular tube or in a circular or tubular shape, the end of the plunger mechanism may have a semi-circular shape formed into the end. Forming the end of the plunger mechanism in this manner enhances the distribution of load over the stent's surface and helps ensure that a secure electrical contact is made between the stent or other device and the mandrel.

Advantageously, the stent may not need to be manually rotated during the electropolishing process. Conventionally, a stent must be rotated to change contact points with an anode mandrel. Otherwise, the stent surface will not be evenly polished. In some embodiments, stent rotation or repositioning may occur naturally, without the need for manually twisting or repositioning the stent. Since the mandrel is smaller than the stent, the stent may move randomly due to natural forces such as fluid flow in the electrolytic bath. As a result, the plunger mechanism can be actuated during the electropolishing process in order to allow the stent to be randomly repositioned. The plunger mechanism, for instance, may be temporarily raised to allow the stent to be repositioned and establish new contact points. While the plunger mechanism is raised, the current to the mandrel may be shut off to avoid arcing or other adverse effects.

Another situation in which embodiments of the electropolishing fixture may be useful is in the electropolishing of relatively long stents. Electropolishing long stents can be challenging because they are more difficult to insert onto mandrels without twisting or damaging the stent or the stents' scaffolding (struts). The loose fit between the anode mandrel of the electropolishing fixture disclosed herein and the stent is useful for longer lengths because the loose fit can reduce such damage. As an example of what may be considered "long", stents with lengths greater than 28 mm may be considered "long" or greater than 23 mm or 18 mm. These example lengths are provided by way of example only and not limitation. More generally, the length of the stent does not impede the ability of embodiments to electropolish the stent. A loose fit ensures that the stent, regardless of length, can be loaded/unloaded from the anode while minimizing damage that may occur, by way of example only, when a friction fit exists between the anode and the stent.

FIG. 1 illustrates a perspective view of an example medical device 100 and is referred to herein as a stent 100. The stent 100 includes a body 110 that is generally tubular in shape, although other shapes and configurations are contemplated. The stent 100 has a first end 102 and a second end 104 that oppose each other, and a lumen 105 passing therethrough. The body 110 includes struts 106 that are arranged to provide, by way of example only, strength and flexibility to the stent 100.

The stent 100 may also have a thickness 114, an inner diameter 116 and an outer diameter 118. The difference between the inner diameter 116 and the outer diameter 118 defines the thickness 114 of the stent 100. Embodiments of the invention can more evenly polish the stent 100 such that at least some dimensions, such as the thickness 114 of the body 110 or the dimensions of the struts 106 are more uniform.

The stent 100 may be made of a material or alloy, including, but not limited to, Nitinol, stainless steel, cobalt chromium, or the like. The stent typically has certain characteristics that facilitate operation of the stent. Some embodiments of the stent 100 (e.g., a stent formed of Nitinol) may be deformed (e.g., bent, compressed, expanded, or the like) by a force. When the force is removed, the stent 100 returns to its original shape. The elasticity and deformability of the stent 100 aid in the deployment of the stent 100 as well as in the operation of the stent 100.

While manufacturing the stent 100, the formation of the struts 106 or of the ends 102, 104 can often results in edges 112 or other areas that are rough or unsmooth. In addition, the thickness 114 may not be uniform, and/or the inner surface and/or outer surface of the stent 100 may be rough.

Electropolishing the stent 100 smoothes the edges 112 as well as the surfaces of the stent 100. Polishing the stent 100 may prevent the stent 100 from having problems during deployment and from causing problems to the vasculature or tissue once deployed. Electropolishing the stent 100 may also make the dimensions of the stent (thickness, strut dimensions, etc.) more uniform.

Figure 2:
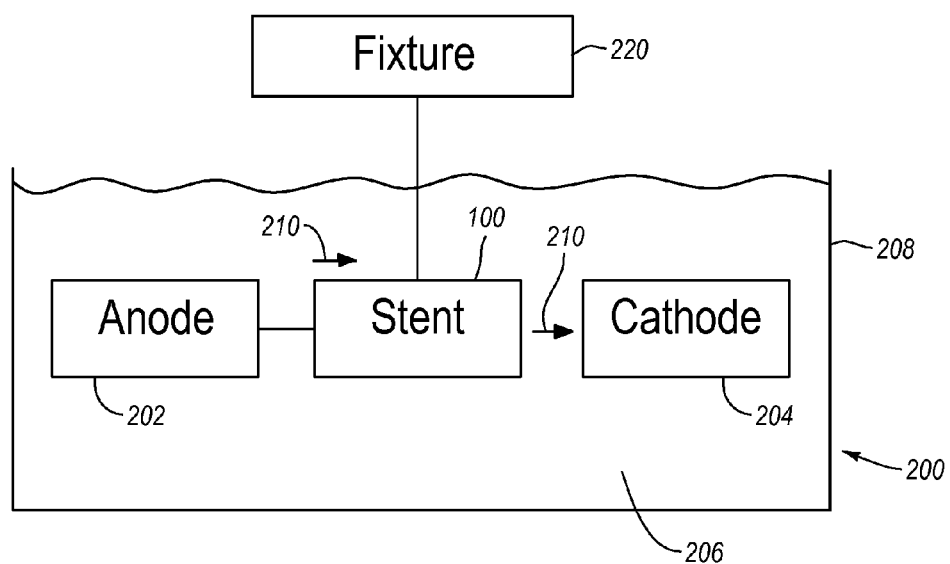
FIG. 2 illustrates a block diagram of an example system for electropolishing an object.

FIG. 2 illustrates a block diagram of an example system 200 for electropolishing the stent 100 or other device. The system 200 includes a container 208 that holds an electrolytic bath 206. The system 200 electropolishes the stent 100 in the electrolytic bath 206 once the stent 100 is loaded on a fixture 220 and immersed in the electrolytic bath 206.

During the electropolishing process, the stent 100 is usually fully immersed in the electrolytic bath 206 along with an anode 202 and a cathode 204. Prior to immersion in the electrolytic bath 206 or after immersion in the electrolytic bath 206, the stent 100 is positioned such that the stent 100 comes into contact with the anode 202. The fixture 220 may be configured such that the stent 100 can be removed from and immersed in the electrolytic bath 206. For example, the stent 100 may be loaded on the anode 202 outside of the electrolytic bath 206 and then immersed for the electropolishing process.

Once the stent 100, the anode 202 and the cathode 204 are immersed in the electrolytic bath 206, a current 210 is then applied. The current 210 flows from the anode 202 to the cathode 204 through the stent 100 and the electrolytic bath 206. In this manner, the stent 100 is electropolished.

More specifically, electropolishing uses electrochemical reactions to remove material from a surface of the stent 100. Electropolishing tends to remove stent material than has increased electrical current densities. Portions of the stent's surface that are rough (bumps, shards, sharp edges, etc.) tend to have higher electrical current densities and are thus removed during the electropolishing process. The surface of the stent 100 is smoothed and polished by the removal of material from the stent's surface.

The fixture 220 included in the system 200 is configured to position the stent 100 within the electrolytic bath 206. The fixture 220 can be controlled automatically and/or manually to position the stent 100 within the electrolytic bath 206. The fixture 220 may be contained wholly or partially within the container 208. The fixture 220 may be configured to be at least partially placed into and lifted out of the electrolytic bath 206 and/or the container 208. For example, the stent 100 is loaded/unloaded when the fixture is lifted to remove the stent 100 from the electrolytic bath 206.

During the electropolishing process performed in the system 200, the stent 100 is typically in contact with an electrode such as the anode 202. As a result, the anode 202 establishes contact points between the anode 202 and the surface of the stent 100. More specifically, the fixture 220 ensures that contact points exist between the anode 202 and an inner surface of the stent 100. The anode 202 can be configured with one or more locations that are configured to contact the stent 100 and the contact points between the anode 202 and the stent 100 can be on an internal surface of the stent 100 and/or an external surface of the stent 100.

Current is supplied to the stent 100 through the anode 202. The cathode 204 is electrically connected with the stent 100 via the electrolytic bath 206. As a result, the current 210 flows to the cathode 204 through the electrolytic bath 206. Current flow from the surface of the stent 100 is facilitated in this manner in order to remove material and thereby smooth the stent surface during the electropolishing process.

Contact points or more generally contact regions corresponding to the locations of contact between the stent 100 and the anode 202 have little or no current flow from the stent surface into the electrolytic bath 206. As a result, the contact points or contact regions are not smoothed or polished in conventional systems or are not smoothed or polished at the same rate as other areas of the stent's surface.

The fixture 220 is configured to position the stent 100 to establish the contact regions between the stent 100 and the anode 202. In addition, the fixture 220 is configured or can be operated such that the stent 100 may be repositioned over time. As a result of being repositioned, the contact regions between the stent 100 an the anode 202 change during the electropolishing process and the overall finish is improved. When the contact regions are exposed after repositioning the stent 100, current is then able to flow from the previous contact regions into the electrolytic bath 206 and to the cathode 204. As a result, the surface of the stent is more evenly smoothed by automatically and/or manually repositioning the stent 100 during the electropolishing process.

In addition, positioning or repositioning the stent 100 can also result in a stent having better or more uniform dimensions. Repositioning the stent 100 can remove bumps or other portions of the stents' surface that may be rough, such as at contact regions, resulting in more even dimensions.

FIG. 2 thus illustrates the stent 100 positioned on the anode 202 or anode contact. The anode 202 is effective to deliver current to the stent 100 during the electropolishing process. In addition, the stent 100 benefits from being repositioned while immersed within the electrolytic bath 206. Repositioning the stent 100 while the stent 100 is immersed prevents the stent 100 from being exposed to a more oxidizing environment and ensures more even erosion of the stent material during the electropolishing process.

Figure 3A:
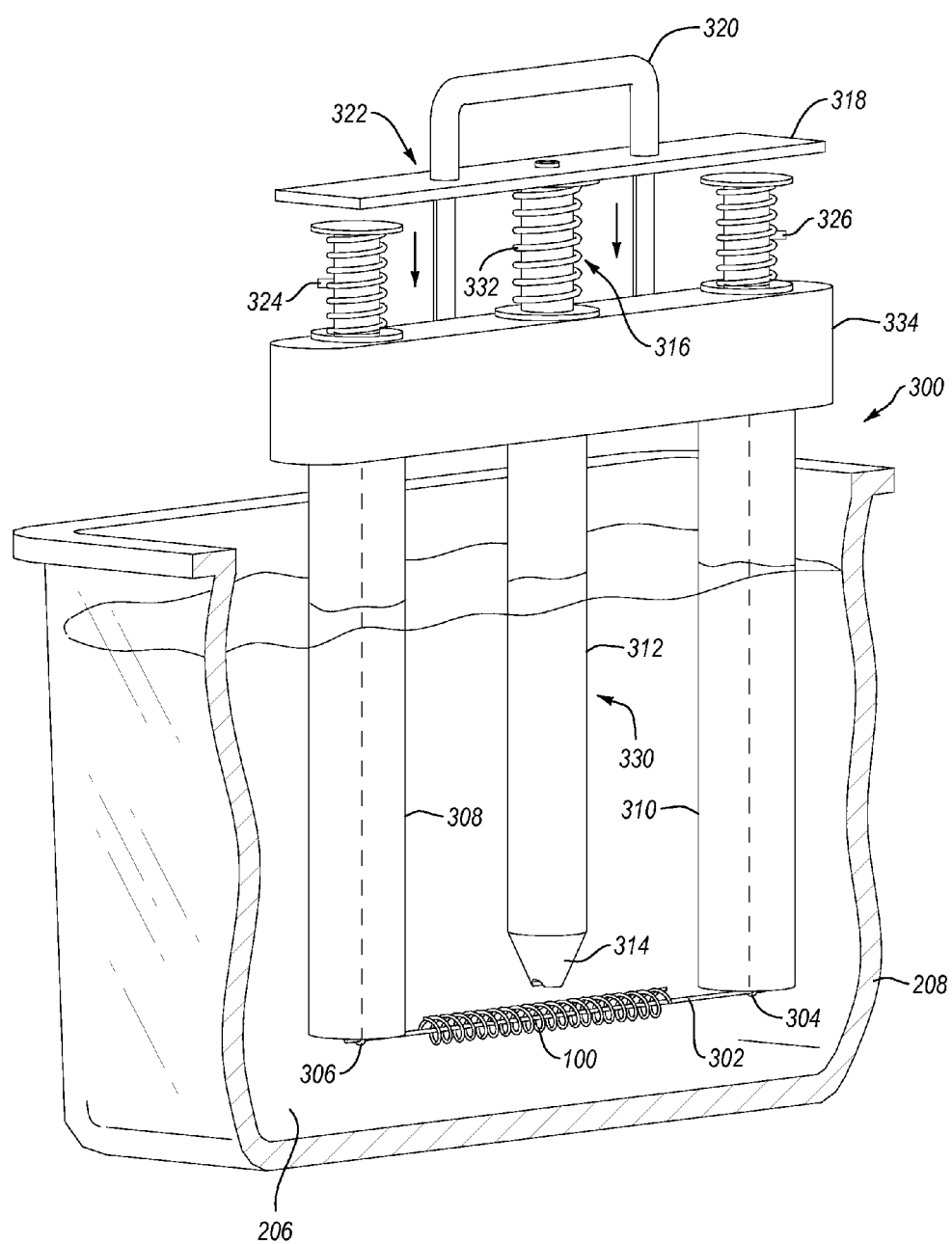
FIG. 3A illustrates an electropolishing fixture that includes a plunger mechanism in a retracted position.
Figure 3B:
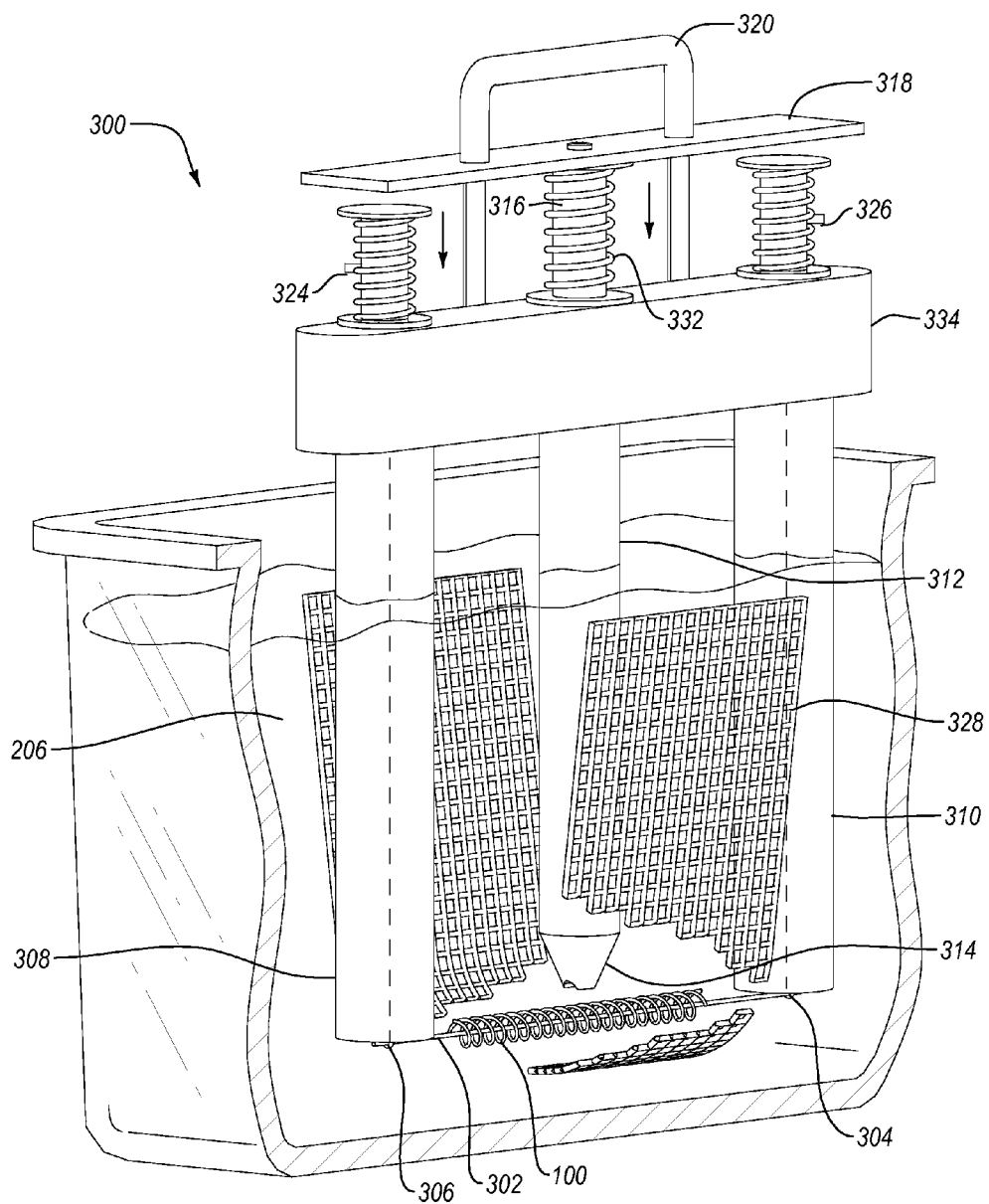
FIG. 3B illustrates the electropolishing fixture of FIG. 3A and further illustrates and a position of a cathode relative to an anode.
Figure 3C:
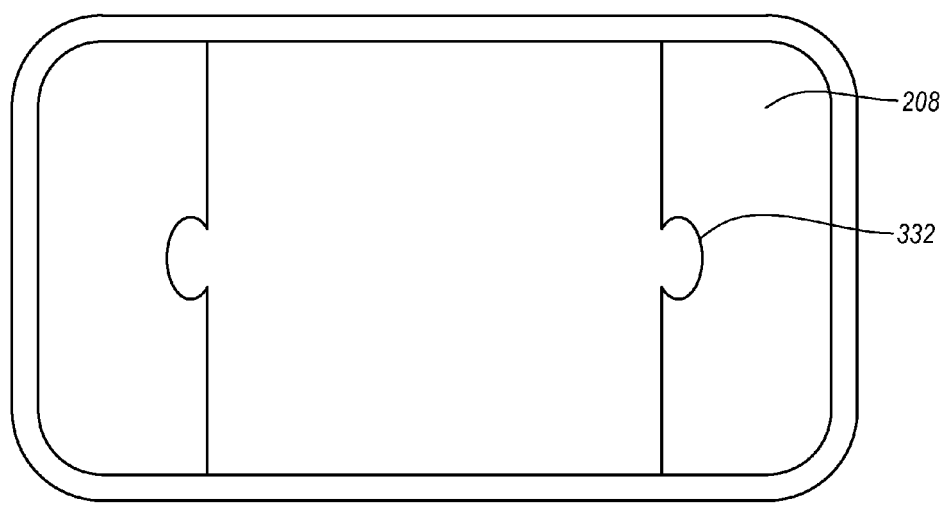
FIG. 3C illustrates a top view of a container that includes guides configured to receive the electropolishing fixture.
Figure 4:
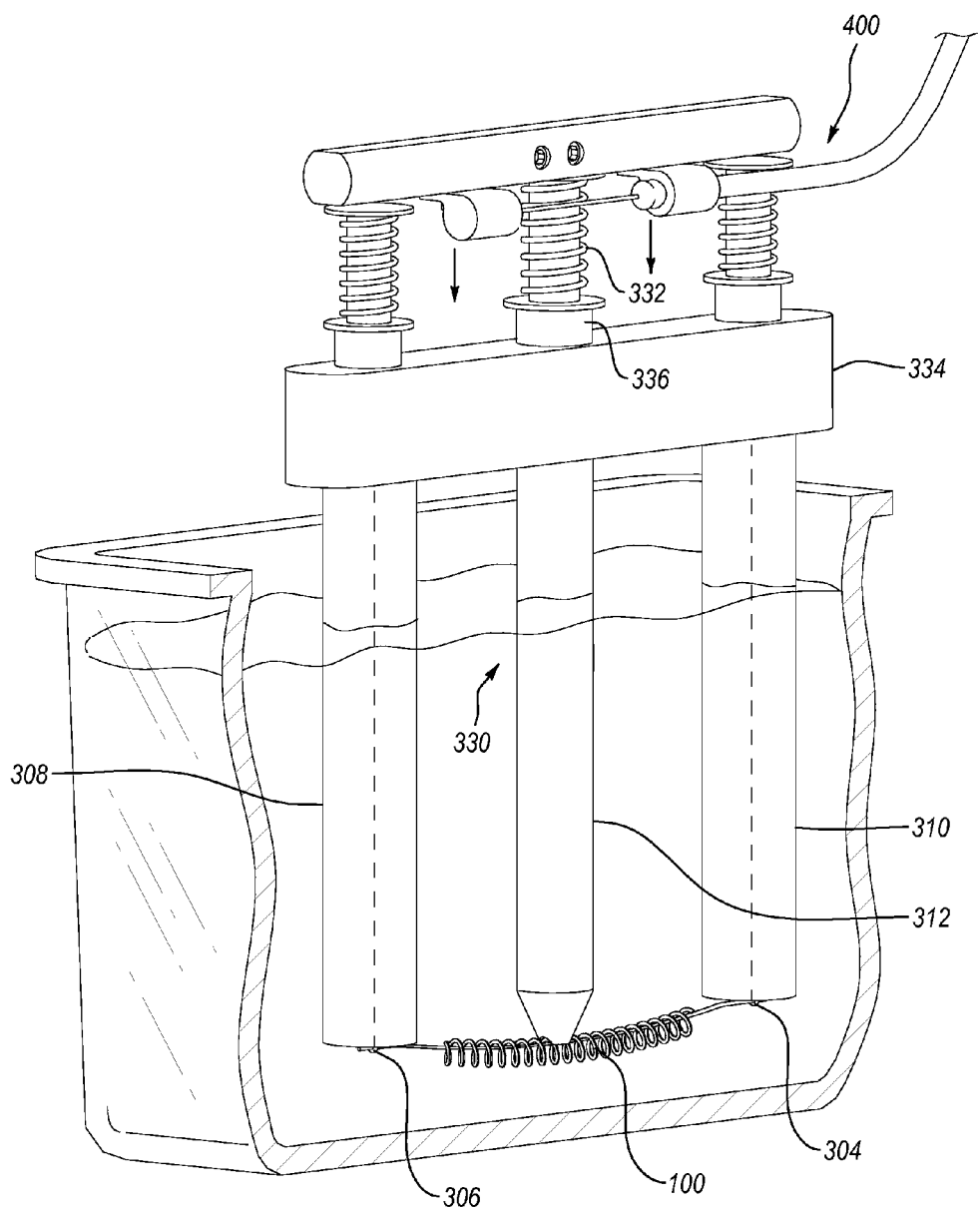
FIG. 4 illustrates the electropolishing fixture of FIG. 3A with the plunger mechanism in an extended position and further illustrates a pneumatic mechanism for operating the plunger mechanism.

FIGS. 3A-4 illustrate an operation of a fixture 300, which is an example of the fixture 220, during an electropolishing process. FIGS. 3A-3B illustrate the fixture 300 in a retracted position prior to or after the electropolishing process. In one example, current is not applied when the fixture 300 is in the retracted position. FIG. 4 illustrates the fixture 300 during the electropolishing process with the fixture 300 in an extended position. In addition to being able to be inserted and removed from an electrolytic bath, the fixture 300 can move between the retracted position and the extended position while the stent is immersed in the electrolytic bath. More specifically, the plunger mechanism of the fixture 300 can be moved from a retracted position (e.g, FIG. 3A) to an extended position (e.g., FIG. 4).

FIG. 3A illustrates an example of an electropolishing fixture 300, or fixture 300, that includes a plunger mechanism 330 in a retracted position. In the retracted position, the plunger mechanism 330 is positioned away from the stent 100 and is not in contact with the stent 100.

FIG. 3A illustrates that the stent 100 is immersed in an electrolytic solution or bath 206. The fixture 300 is configured to establish electrical contact between an electrode (e.g., an anode 302) and the stent 100. The plunger mechanism 330 cooperates with an actuator 322 to establish the electrical contact. Once electrical contact is established, electropolishing of the stent 100 can occur.

In FIG. 3A, the anode 302 is connected to a pair of posts (a post 308 and a post 310). Each of the posts 308 and 310 may be formed of an insulator and may have a conductive center. A contact 306 extends from an end of the post 308 and a contact 304 extends from an end of the post 310. The anode 302 can be permanently connected to one of the contacts 304, 306, but is not required. Alternatively, the anode 302 can be removably connected with one or both of the contacts 304 and 306. The contacts 304 and/or 306 may be spring loaded in order to establish a tension in the anode 302 when the anode 302 is connected to the contacts 304 and 306.

The stent 100 is typically placed on the anode 302 by removing the anode from, for instance, the contact 304 and sliding the anode 302 through the lumen 105 of the stent 100. The anode 302 can then be reconnected to the contact 304. The contacts 304 and 306 pass through, respectively, the posts 310 and 308 such that the anode 302 can be connected to an appropriate electrical source via the contacts 324 and 326 that are outside of the bath 206 and positioned on an upper end of the posts 308 and 310. The connection with the electrical source can be a single point of contact if all of the components are electrically conductive. For example, the electrical connection may be achieved with only the contact 324.

The fixture 300 includes a plunger mechanism 330 that cooperates with an actuator 322 to move the plunger mechanism 330 between the retracted position shown in FIGS. 3A-3B and the extended position shown in FIG. 4.

The plunger mechanism 330 includes a body 312 having a proximal end 316 and a distal end 314 relative to the actuator 322. The plunger mechanism 330 is typically formed of a non-conductive material and may be spring loaded or otherwise biased. In one example, application of an actuating force is required to cause the plunger mechanism 330 to make contact with the stent 100. The plunger mechanism 330 automatically returns to the retracted position from the extended position when the actuating force is removed. The proximal end 316 may have a cross sectional shape (e.g., larger, smaller, different configuration) that is different from a cross sectional shape of the body 312. The distal end 314 may taper down from the body 312 and be configured receive a shape of the stent 100.

The actuator 322 may include a plate 318 that has a handle 320. A user may grasp the handle 320 and pull/push or otherwise move the handle 320 to cause the plate 318 to contact the proximal end 316 of the plunger mechanism 324. This actuating force causes the plunger mechanism 324 to move towards the stent 100.

The plate 318 may be spring mounted, pivotally mounted or the like. A spring 332 may bias the plunger mechanism 330 against the actuating force applied by the actuator 322. More specifically, the plunger mechanism 330 may be spring loaded such that when a force applied by the plate 318 is removed, the spring acts to push the plunger mechanisms 330 away from the stent 100. Alternatively, the plate 318 may be mechanically connected to the proximal end 316 such that movement of the handle 320 results in a corresponding movement of the plunger mechanism 314.

FIG. 3C illustrates a top view of the container and illustrates guides for receiving the fixture. More specifically, the container 208 may be configured with guides 332 that are configured to receive the posts 308 and 310 of the fixture 300. The guides 332 may be an integral part of the container 208 and can help maintain tension in the anode 302 when the anode 302 is connected with the posts 308 and 310

FIG. 3B illustrates the electropolishing fixture of FIG. 3A and further illustrates a position of a cathode 328 relative to the anode 302. The cathode 328 can be placed in the electrolytic bath 206 such that the cathode 328 substantially surrounds the stent 100 when the stent 100 is immersed. The cathode 328 is configured or placed such that the cathode 328 does not physically touch the stent 100. As a result, current flows to the cathode 328 through the bath 206. In addition, the cathode 328 is configured such that the current can emanate from substantially all of the stent's surface, which improves the electropolishing process.

In this manner, the electropolishing process can occur as current flows from the anode through the stent 100 and the electrolytic bath 206 to the cathode 328. The cathode 328 may be a metal mesh and can be arranged in multiple manners within the electrolytic bath 206. The cathode 328 may also be connected to a source or to ground as necessary.

The fixture 300 also includes a bar 334. The bar 334 is configured such that the posts 308 and 310 extend distally. A proximal end of the posts 308 and 310 may extend distally. The posts 308 and 310 are typically solid and do not move relative to the bar 334. The bar 334 includes an opening 336 configured to receive the plunger mechanism 330. The plunger 334 and more specifically the body 312 can be slidably moved inside the opening 336 such that the plunger mechanism 330 can be moved between the extended position and the retracted position. A proximal end 316 may also include a stop that cooperates with the opening 336 to place a limit on which the plunger mechanism 330 may be moved. The stop, for example, may prevent the plunger mechanism 330 from pressing against the stent 100 with too much force such that the stent 100, anode 302, or fixture is damaged.

FIG. 4 illustrates the electropolishing fixture of FIG. 3A with the plunger mechanism 330 in an extended position and further illustrates an actuator 400 for operating the plunger mechanism 330. The actuator 400 is another example of an actuator and may be, for example, a pneumatic mechanism that can push or move the plunger mechanism 330 from one position to another position. The spring 332 may lift the plunger mechanism 330 after the actuating force is removed.

When the actuator 400 is actuated, the plunger mechanism 330 is moved towards the stent 100 as illustrated in FIG. 4. The distal end 314 typically makes contact with the stent 100 and may push against the stent 100 with sufficient force to establish contact between an interior surface of the stent 100 and the anode 302. The anode 302 may be slightly bowed, which ensures sufficient contact. The guides 332 may prevent the posts 308 and 310 from moving towards each other and thus maintain tension in the anode 302.

Because the plunger mechanism 330 is used to establish electrical contact between the anode 302 and the stent 100, the anode 302 may have a simple shape and need not have bends or other configurations that conventionally establish electrical contact. The mandrel or anode 302 may be a straight, cylindrically shaped wire, for example of a suitable conductive material. The mandrel or anode 302 may also be a coiled or spiral wire. The mandrel or anode 302 may have a relatively constant cross section along its length or the cross section may change along its length. For instance, the mandrel or anode 302 may be tapered or decrease in cross section towards the middle, or the like.

The fixture 300 enables the stent 100 to have a longer length that can be easily mounted on the anode 302 prior to the electropolishing process and easily removed from the anode 302 when the electropolishing process is completed. Because the anode 302 has a loose fit, the anode 302 does not substantially resist the loading or unloading the stent 100. As a result, the struts are less likely to be bent, scratched, or otherwise damaged. Further, this is advantageously useful for stents having thinner stents or stents that are comparatively long. The plunger mechanism 330 may be substantially non-conductive. The plunger mechanism or other aspects of the invention may be formed using non-conductive and/or chemically resistant materials (e.g., acid/EP electrolyte resistant polymer). PTFE, FEP, PVDF, ECTFE, PE, PP or the like, or other fluoro-polymers, glss, and ceramics are examples of material that may be used at least in the plunger mechanism.

The actuator 400 may be mounted to the proximal ends of the posts 308 and 310. As a result, the actuator 400 causes the plunger mechanism 330 to move relative to the posts 308 and 310. The actuator 400 or other actuator may be pneumatically driven, electrically driven, magnetically driven or the like. The actuator 400 may be automatically controlled by a controller or other processing device. As previously stated, the actuator 400 shown in FIG. 4 may be a pneumatically driven actuator 400. The controller can generate the appropriate signals to operate the actuator 330 such that the plunger mechanism is moved as necessary between the retracted position and the extended position.

Figure 5:
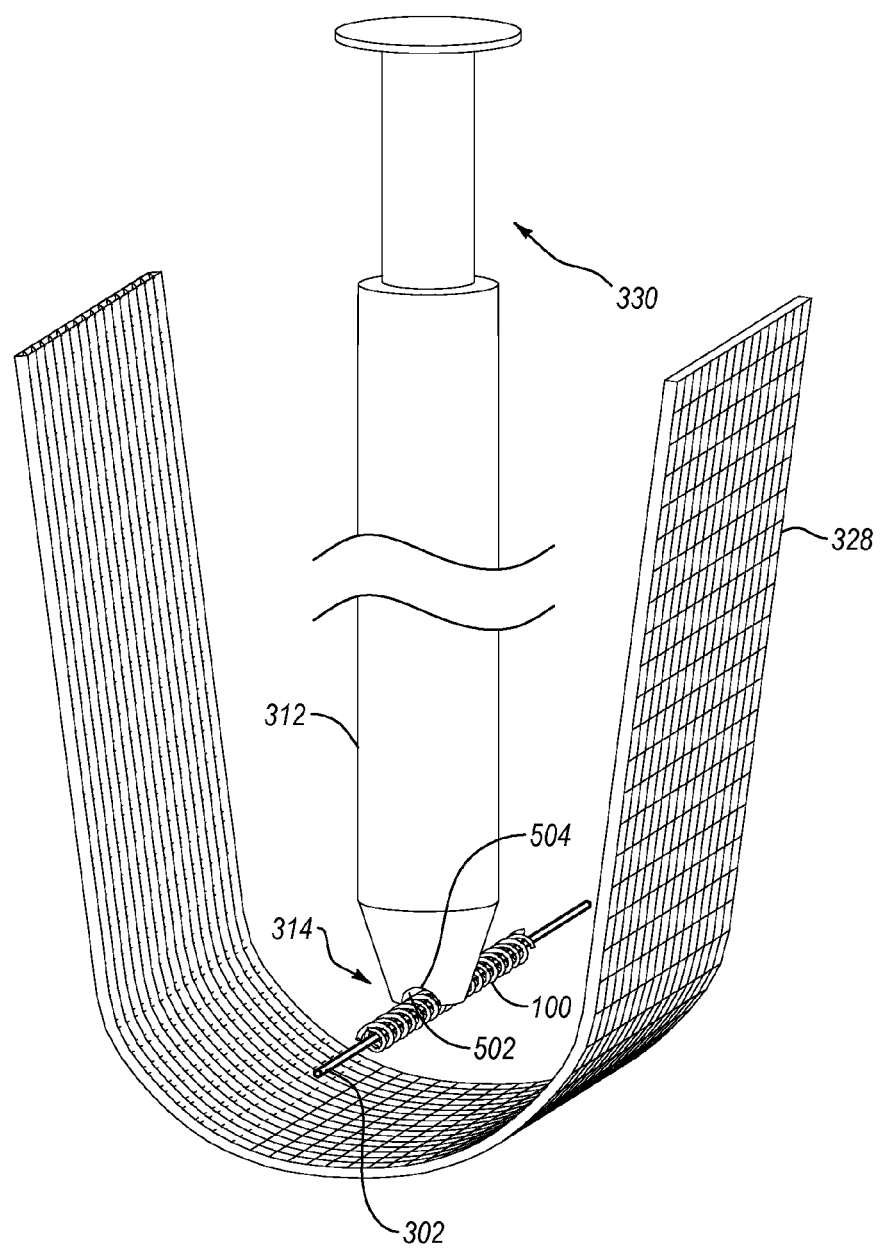
FIG. 5 illustrates a perspective view of a notch formed in a distal end of the plunger mechanism.

FIG. 5 illustrates a perspective view of the plunger mechanism 330 in the extended position. FIG. 5 illustrates that the distal end 314 includes a notch 502 shaped to receive the stent 100. The notch 502 may have an arc shape that may have a radius selected for specific stents or that is selected according to the device being electropolished. The arc may be another shape (e.g., elliptical) to control how the notch 502 contacts the stent 100. When the plunger mechanism 330 is moved to the extended position, a top 504 of the notch (and/or sides of the notch 502) comes into contact with the stent 100 and pushes the stent 100 against the anode 302. The anode 302 is connected to the contacts 304 and 306 (see FIG. 4) with sufficient tension to ensure that reliable electrical contact can be established between the stent 100 and the anode 302 when the plunger mechanism 330 is actuated.

In this example, the sides of the notch 502 effectively constrain lateral movement of the stent 100 during the electropolishing process. This prevents the stent 100, for instance, from slipping up on a side of the body 312 of the plunger mechanism 330 and potentially hindering the electropolishing process. During the electropolishing process, the electrolytic bath may be agitated in a manner that, but for the notch 502, may displace the stent 100 relative to the distal end 314 of the plunger mechanism 330.

In addition, the agitation of the bath during the electropolishing process may be used to reposition the stent 100. As a result, contact points between the stent 100 and the anode 302 are exposed as new contact points are established and the electropolishing process is performed more uniformly with respect to the surface of the stent 100. In one example, lifting and then lowering the plunger mechanism 330 may be sufficient to allow the stent 100 to be repositioned within the electrolytic bath.

Figure 6:
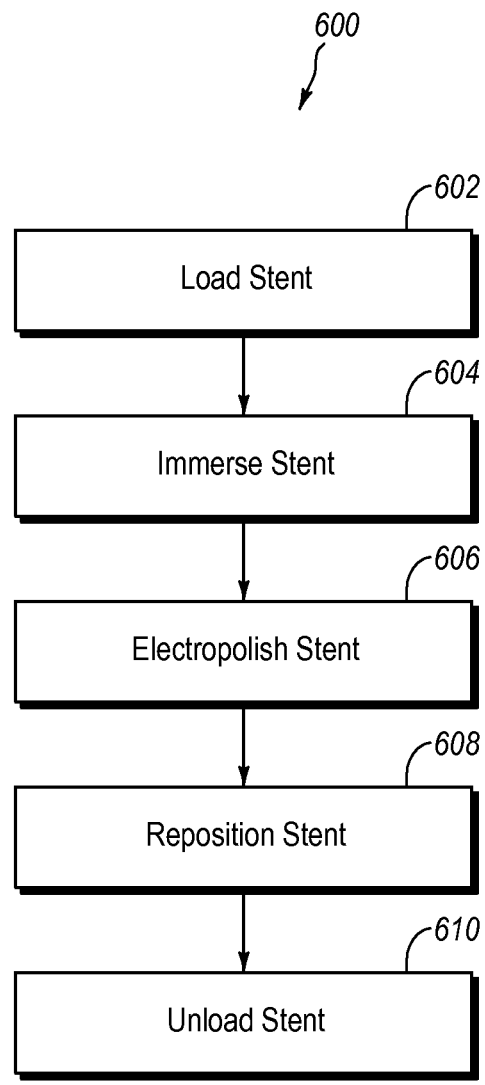
FIG. 6 illustrates an example of a method for electropolishing a device such as a stent.

FIG. 6 illustrates an example of a method 600 for electropolishing a device such as a stent. In box 602, a device such as a stent is loaded on the electropolishing fixture. This may include disconnecting the anode from the posts, placing the stent on the anode and then reconnecting the stent. In box 604, the fixture is lowered such that the stent is immersed in the electrolytic bath. In box 606, the stent is electropolished. This may include generating an actuating force in order to move the plunger mechanism to the extended position in order to establish contact between the stent and the anode. A current flowing through the stent is part of this process.

In box 608, the stent is optionally repositioned. Repositioning the stent may include retracting the plunger mechanism such that the flow of fluid in the electrolytic batch repositions the stent and then extending the plunger mechanism in order to reestablish contact. Current may or may not flow while the stent is repositioned.

In box 610, the stent is unloaded. This can include retracting the fixture from the bath, disconnecting the anode from the posts and sliding the electropolished stent off of the anode.

The electropolishing fixture disclosed herein can be configured to accommodate multiple stents. Multiple stents could be loaded on the same anode. In this case, the plunger mechanism could have a wide width to accommodate multiple stents, or multiple plunger mechanisms 330 can be used on the same stent 100 or other device being electropolished. Alternatively, multiple fixtures can be operated at the same time under the same controller or server computer. In addition, the anode can be configured to accommodate a shape of the device being electropolished. A "Y" shaped anode, for instance, could be used in a "Y" shaped stent or device. A PLC controller is an example of a controller that may be used to control aspects of the electropolishing fixtures or for controlling actuators or the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An electropolishing fixture for electropolishing a stent, the fixture comprising:
   a first post;
   a second post, connected to the first post by a bar, the first post and the second post extending distally from the bar;
   an electrode removably connected between the first post and the second post, wherein the stent is loaded on the electrode;
   an actuator; and
   a plunger mechanism having a proximal end, a distal end configured to receive the stent, a body between the proximal end and the distal end, and a stop that cooperate with the bar to limit movement of the plunger mechanism in at least one direction, wherein the actuator cooperates with the proximal end of the plunger mechanism to move the plunger mechanism from a retracted position to an extended position, wherein the distal end engages the stent and presses the stent against the electrode in the extended position to establish an electrical contact between the stent and the electrode and the plunger body extends through a hole in the bar that guides movement of the plunger mechanism between the extended position and the retracted position.

2. The fixture of claim 1, wherein the first post is placed on a first side of the plunger mechanism and the second post is placed on a second side of the plunger mechanism.

3. The fixture of claim 2, wherein the bar holds the first post and the second post in position relative to the plunger mechanism.

4. The fixture of claim 1, wherein the bar includes an opening formed in a center portion, the opening configured to slidably receive a body of the plunger mechanism.

5. The fixture of claim 4, wherein the opening guides movement of the plunger mechanism between the retracted position and the extended position.

6. The fixture of claim 2, wherein the first post and/or the second post each comprise a contact that provides a connection to an electrical source, the contacts configured to removably connect with the electrode.

7. The fixture of claim 6, wherein the electrode is configured to loosely fit inside of the stent when the electrode is connected with the contacts and the stent is loaded on the electrode, wherein the electrical contact between the stent and the electrode is established when the distal end of the plunger mechanism presses the stent against the electrode and wherein a contact point for the electrical contact is changeable by retracting the plunger mechanism and then extending the plunger mechanism.

8. The fixture of claim 6, wherein the contacts are configured to maintain a tension in the electrode.

9. The fixture of claim 6, wherein the actuator is manually controlled, automatically controlled by a computer, or controlled by a PLC controller.

10. The fixture of claim 6, wherein the distal end of the plunger mechanism includes a notch shaped to receive the stent.

11. The fixture of claim 9, wherein the computer retracts and extends the plunger mechanism to reposition the stent on the electrode.

12. An electropolishing fixture for use in electropolishing a device in an electrolytic bath, the electropolishing fixture comprising:
    an actuator;
    a non-conductive first post having a first contact and a non-conductive second post having a second contact, wherein the first post and the second post are chemically resistant to the electrolytic bath;
    an electrode removably connected with at least one of the first contact and the second contact, the electrode configured to receive the device so that the device is loaded on the electrode during the electropolishing process;
    a plunger mechanism that cooperates to move between a retracted position and an extended position relative to the device loaded on the electrode, wherein the plunger device presses against the device while the device is loaded on the electrode and immersed in the electrolytic bath in the extended position to establish electrical contact between the device and the electrode during the electropolishing process; and
    a bar, wherein the first and second posts extend distally from the bar and are permanently connected to the bar, wherein the bar includes an opening configured to slidably receive a body of the plunger mechanism, wherein the opening guides movement of the plunger mechanism between the extended position and the retracted position.

13. The electropolishing fixture of claim 12, wherein the actuator comprises a manual actuator, a pneumatic actuator, a magnetic actuator, or an electric actuator.

14. The electropolishing fixture of claim 12, wherein the actuator generates an actuating force that is applied to the plunger mechanism to move the plunger mechanism towards the device.

15. The electropolishing fixture of claim 14, wherein the actuator acts on a proximal end of the plunger mechanism, wherein a distal end of the actuator presses against the device.

16. The electropolishing fixture of claim 12, wherein the plunger mechanism comprises a distal end configured to engage a surface of the device and to constrain lateral movement of the device.

17. The electropolishing fixture of claim 16, wherein the distal end comprises a notch that receives the device when the plunger mechanism is in the extended position.

18. The electropolishing fixture of claim 12, wherein a proximal end of the plunger mechanism is spring loaded such that the plunger mechanism returns to the retracted position when an actuating force applied by the actuator is removed.

19. The electropolishing fixture of claim 12, wherein the device is a stent and the electrode is an anode, wherein the stent is loaded on the anode by passing the anode through a lumen of the stent, wherein the anode has dimensions that are smaller than the inner diameter of the stent.

20. The electropolishing fixture of claim 12, wherein the plunger mechanism includes a stop that cooperates with the bar to limit movement of the plunger mechanism in at least one direction.

21. The electropolishing fixture of claim 12, wherein the first and second posts and the plunger mechanism are insulators, wherein a conductor passes through an interior of the first and second posts for connection to an electrical source.

22. A method for electropolishing a stent, the method comprising:
   loading the stent on an anode in an electropolishing fixture, the electropolishing fixture comprising:
      a non-conductive first post having a first contact and a non-conductive second post having a second contact, wherein the first post and the second post are chemically resistant to an electrolytic bath
      an electrode removably connected with at least one of the first contact and the second contact, the electrode configured to receive the device so that the device is loaded on the electrode during the electropolishing process;
      a plunger mechanism that cooperates to move between a retracted position and an extended position relative to the device loaded on the electrode, wherein the plunger device presses against the device while the device is loaded on the electrode and immersed in the electrolytic bath in the extended position to establish electrical contact between the device and the electrode during the electropolishing process; and
      a bar, wherein the first and second posts extend distally from the bar and are permanently connected to the bar, wherein the bar includes an opening configured to slidably receive a body of the plunger mechanism, wherein the opening guides movement of the plunger mechanism between the extended position and the retracted position;
   immersing the stent in the electrolytic bath;
   moving the plunger mechanism of the electropolishing fixture to the extended position to establish electrical contact between the stent and the anode;
   electropolishing the stent; and
   removing the stent from the electrolytic bath and unloading the stent from the anode.

23. The method of claim 22, further comprising repositioning the stent on the anode by:
   retracting so as to allow the stent to move relative to the anode; and
   re-extending the plunger mechanism to reestablish electrical contact between the stent and the anode.

24. The method of claim 22, further comprising agitating the electrolytic bath.

* * * * *

UNITED STATES PATENT AND TRADEMARK OFFICE
CERTIFICATE OF CORRECTION

| | | |
|---|---|---|
| PATENT NO. | : 8,815,061 B2 | Page 1 of 1 |
| APPLICATION NO. | : 13/618348 | |
| DATED | : August 26, 2014 | |
| INVENTOR(S) | : Andreacchi et al. | |

It is certified that error appears in the above-identified patent and that said Letters Patent is hereby corrected as shown below:

Title Page,

Item (75), Inventors, change Sophia L. Wong, Milipitas, CA (US) to Sophia L. Wong, Milpitas, CA (US)

Signed and Sealed this
Thirty-first Day of March, 2015

Michelle K. Lee
*Director of the United States Patent and Trademark Office*